(12) United States Patent
Meridew

(10) Patent No.: US 9,393,030 B2
(45) Date of Patent: Jul. 19, 2016

(54) MICROFRACTURE PICK FOR FEMORAL HEAD

(71) Applicant: Biomet Manufacturing, LLC, Warsaw, IN (US)

(72) Inventor: Jason D. Meridew, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 164 days.

(21) Appl. No.: 14/257,303

(22) Filed: Apr. 21, 2014

(65) Prior Publication Data

US 2014/0228850 A1 Aug. 14, 2014

Related U.S. Application Data

(63) Continuation of application No. 13/107,387, filed on May 13, 2011, now Pat. No. 8,721,648.

(51) Int. Cl.
| A61B 17/16 | (2006.01) |
| --- | --- |
| A61B 17/56 | (2006.01) |
| A61B 17/17 | (2006.01) |

(52) U.S. Cl.
CPC ......... *A61B 17/1668* (2013.01); *A61B 17/1604* (2013.01); *A61B 17/1664* (2013.01); *A61B 17/1666* (2013.01); *A61B 17/1675* (2013.01); *A61B 17/1742* (2013.01); *A61B 17/56* (2013.01); *A61B 2017/564* (2013.01)

(58) Field of Classification Search
CPC ........... A61B 17/1604; A61B 17/1664; A61B 17/1666; A61B 17/1668; A61B 17/1742; A61B 17/56; A61B 2017/564
See application file for complete search history.

(56) References Cited

U.S. PATENT DOCUMENTS

| 4,211,446 | A | 7/1980 | Shultz, Sr. |
| 5,245,737 | A | 9/1993 | Perea |
| 6,319,272 | B1 | 11/2001 | Brenneman et al. |
| 6,423,073 | B2 | 7/2002 | Bowman |
| 6,482,237 | B2 | 11/2002 | Mosseri |
| 6,960,214 | B2 | 11/2005 | Burkinshaw |
| 8,409,230 | B2 | 4/2013 | Pamichev et al. |
| 8,721,648 | B2 | 5/2014 | Meridew |
| 2006/0085006 | A1 | 4/2006 | Ek et al. |
| 2006/0235419 | A1 | 10/2006 | Steinwachs et al. |
| 2007/0270870 | A1 | 11/2007 | Torrie et al. |
| 2010/0191195 | A1 | 7/2010 | Kirschenbaum |
| 2010/0249786 | A1* | 9/2010 | Schmieding ....... A61B 17/1633 606/80 |
| 2012/0071876 | A1* | 3/2012 | Stoll .................. A61B 17/1604 606/79 |

OTHER PUBLICATIONS

Kelly et al., "Hip Arthroscopy Update", Hospital for Special Surgery, vol. 1, pp. 40-48, 2005.

* cited by examiner

*Primary Examiner* — Larry E Waggle, Jr.
(74) *Attorney, Agent, or Firm* — Schwegman Lundberg & Woessner, P.A.

(57) ABSTRACT

The present teachings provide one or more surgical implements for repairing damaged tissue, such as cartilage on the femoral head. A microfracture pick system for repairing cartilage on a femoral head is provided. The system can include a handle having a proximal end and a distal end. The system can also include an arcuate arm shaped to extend from the distal end of the handle and adapted to extend around the femoral head. The arcuate arm can have a distal tip extending toward the handle along a longitudinal axis of the handle. The system can also include an impaction member at the proximal end of the handle.

20 Claims, 3 Drawing Sheets

MICROFRACTURE PICK FOR FEMORAL HEAD

CROSS-REFERENCE TO RELATED APPLICATIONS

This application is a continuation of U.S. patent application Ser. No. 13/107,387 filed on May 13, 2011. The entire disclosure of the above application is incorporated herein by reference.

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function or repair the damaged tissue. Surgical intervention can include any surgical procedure that can restore function to the damaged tissue or that can repair the damaged tissue. In one example, a surgical intervention can include the use of one or more surgical instruments to aid in repairing the damaged tissue.

The present disclosure relates to surgical instruments for use in repairing cartilage on a femoral head, and more specifically relates to a microfracture pick for a femoral head.

SUMMARY

According to various aspects, provided is a microfracture pick system for repairing cartilage on a femoral head. The system can include a handle having a proximal end and a distal end. The system can also include an arcuate arm shaped to extend from the distal end of the handle and adapted to extend around the femoral head. The arcuate arm can have a distal tip extending toward the handle along a longitudinal axis of the handle. The system can also include an impaction member at the proximal end of the handle.

Further provided is a microfracture pick system for repairing cartilage on a femoral head. The system can include a handle having a proximal end and a distal end, and an arm having a proximal end coupled to the distal end of the handle. The arm can have a distal tip extending toward the handle along a longitudinal axis of the handle. The arm can define a slot and a bore in communication with the slot, the bore defined from the slot to the distal tip. The system can also include a retractable tip slidably received in the bore. A portion of the retractable tip can extend through the slot and can be operable to move the retractable tip from a first position to a second position. The system can include an impaction member coupled to the proximal end of the handle.

Additionally, provided is a method for repairing cartilage on a femoral head. The method can include making an incision in an anatomy near a femoral head. The method can also include inserting a pick through the incision so that a distal tip of an arcuate arm is positioned near an articulating surface of the femoral head. The pick can have a handle and the arcuate arm can be coupled to the handle. The arcuate arm can have the distal tip extending toward the handle along a longitudinal axis of the handle. The method can include impacting a impaction member coupled to an end of the handle such that a force from the impact causes the distal tip to create a hole in the femoral head.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

DESCRIPTION OF VARIOUS ASPECTS

Figure 1:
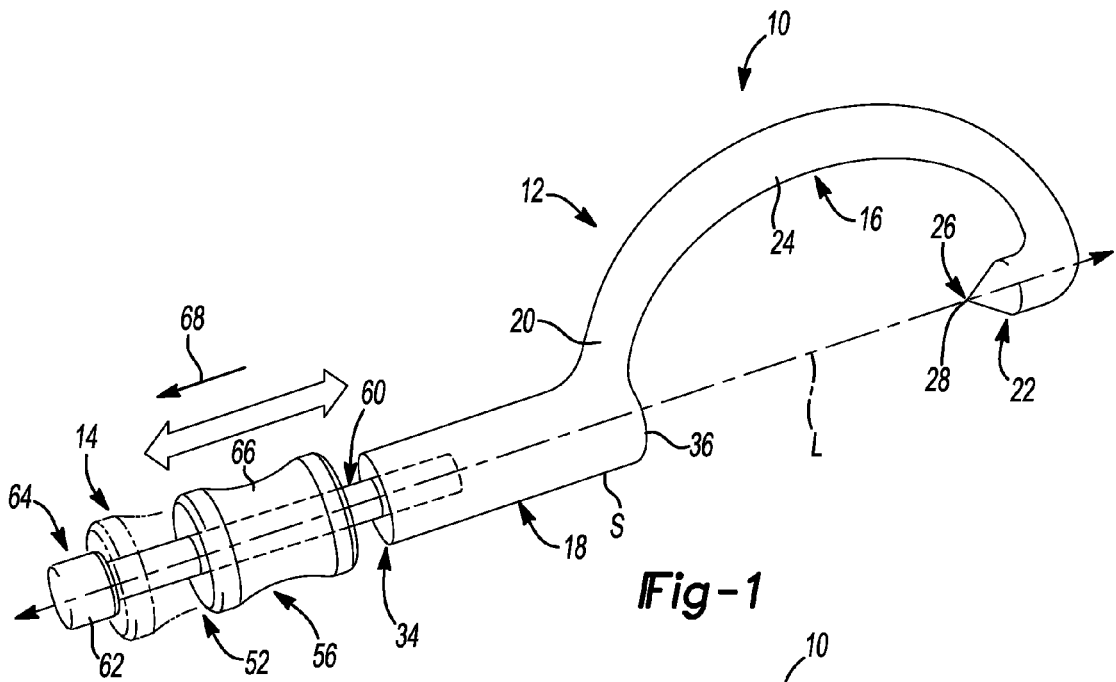
FIG. 1 is a perspective view of an exemplary microfracture pick system for use with a femoral head according to the present teachings.

The following description is merely exemplary in nature and is not intended to limit the present teachings, application, or uses. It should be understood that throughout the drawings, corresponding reference numerals indicate like or corresponding parts and features. Although the following description is related generally to a system for use in an anatomy to repair damaged tissue, such as cartilage associated with the femoral head, it will be understood that the system as described and claimed herein can be used in any appropriate surgical procedure, such to repair cartilage of the humeral head. Further, it will be understood that the drawings are for illustration purposes only, and are not to scale. Therefore, it will be understood that the following discussions are not intended to limit the scope of the present teachings and claims herein.

Figure 2:
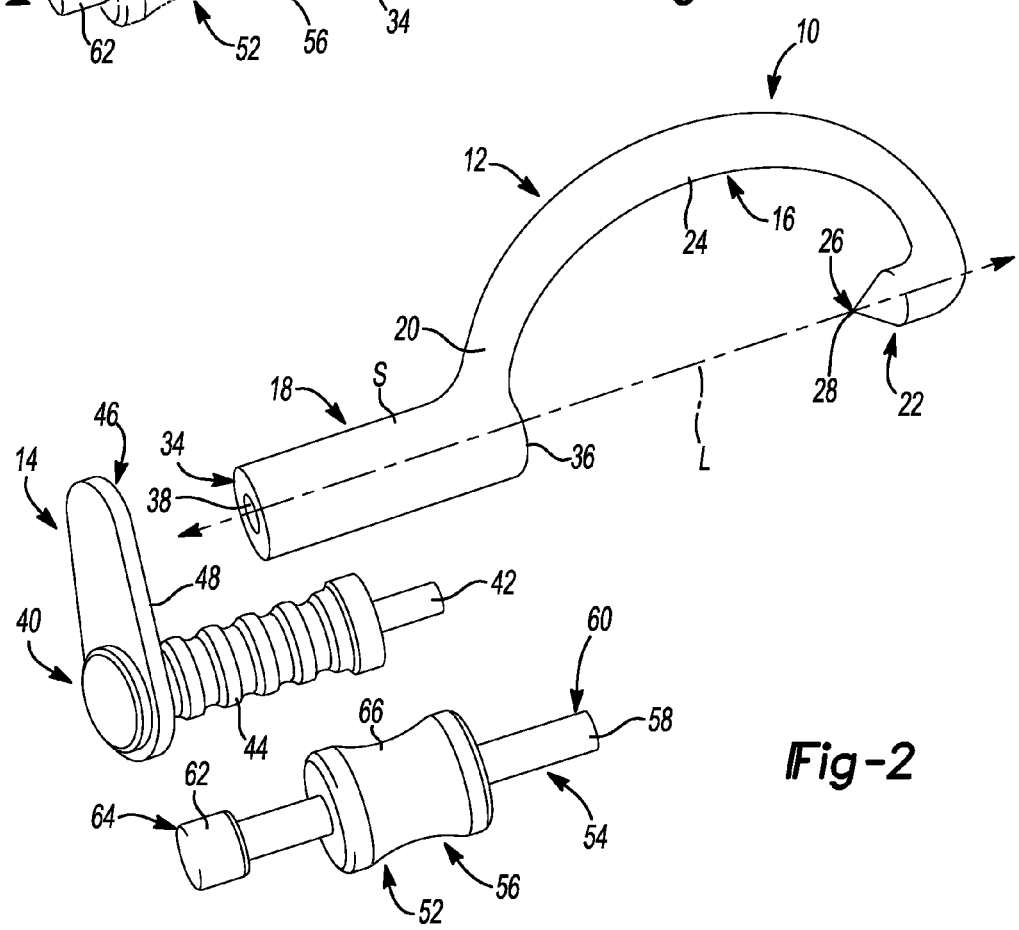
FIG. 2 is a disassembled view of the microfracture pick system of FIG. 1.
Figure 3:
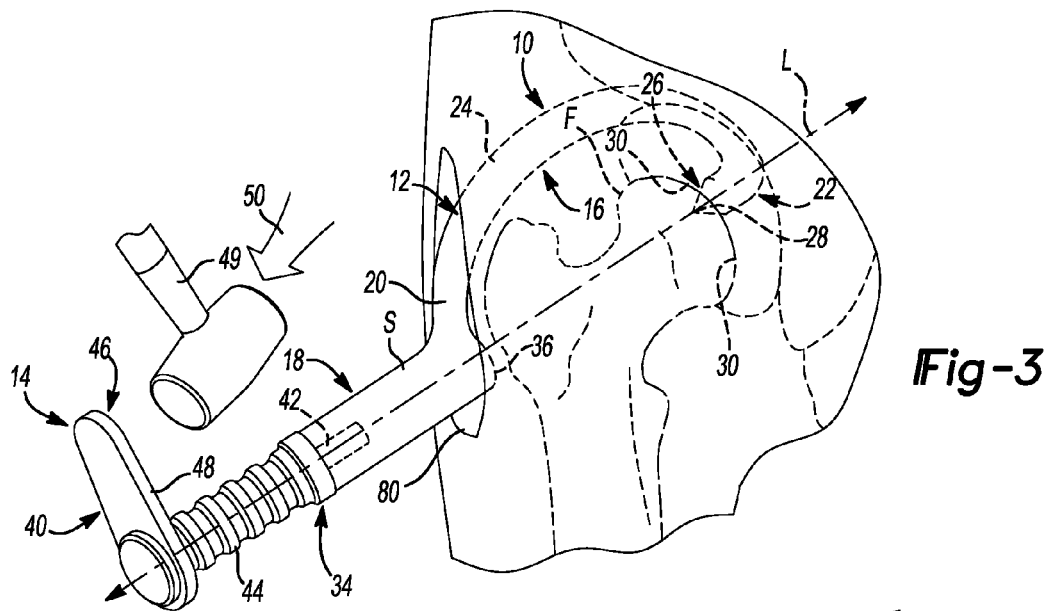
FIG. 3 is a schematic environmental illustration of the microfracture pick system of FIG. 1 being used to perform a procedure on a femoral head.

With reference to FIGS. 1-3, a microfracture pick system 10 is shown. The microfracture pick system 10 may be particularly adapted for repairing cartilage on a femoral head F (FIG. 3). Various aspects of the present teachings, however, may have application for other procedures. In certain applications, with reference to FIG. 3, the microfracture pick system 10 can be inserted into the anatomy such that a portion of the microfracture pick system 10 is adjacent to the femoral head F to create one or more small holes in the femoral head F, as will be discussed in greater detail herein. With reference to FIGS. 1-3, the microfracture pick system 10 can include a pick 12 and at least one impaction member 14.

The pick 12 can include a member or arcuate arm 16 and a graspable portion or handle 18. The pick 12 can be composed of any suitable biocompatible material, such as a biocompatible metal or polymer. For example, the pick 12 can be composed of a stainless steel. In one example, the arm 16 can be integrally formed as one unitary piece (e.g. via casting) with the handle 18. It should be noted, however, that the arm 16 and the handle 18 could be discretely formed and coupled via any suitable technique, such as the use of mechanical fasteners, threading the arm 16 into an internally threaded bore on the handle 18 or vice versa, welding, etc.

The arm 16 can be shaped to fit around the femoral head F. The arm 16 can include a proximal end 20, a distal end 22 and an arcuate portion 24 between the proximal end 20 and the distal end 22. The proximal end 20 can be coupled to the handle 18. The distal end 22 can be positioned opposite the proximal end 20 and can lie along a longitudinal axis L of the handle 18. The distal end 22 can include a distal tip 26. The distal tip 26 can be directed inward, towards the handle 18 and can be aligned with the longitudinal axis L. The distal tip 26 can taper to a point 28. The point 28 can be used to form small holes 30 in the femoral head F (FIG. 3). Generally, the distal tip 26 can be sized such that the distal tip 26 forms the holes 30 in the femoral head F with about a 2.0 millimeter (mm) to about a 3.0 millimeter (mm) diameter. In one example, the distal tip 26 can taper from the point 28 to an effective diameter of about 2.0 millimeter (mm) to about 3.0 millimeter (mm), and yet taper wider than this. The effective diameter can be defined as the diameter at the surface of the anatomy when the distal tip 26 is driven into the anatomy. Further, it should be noted, however, that the distal tip 26 can have any selected diameter to form any selected diameter hole 30, such as a diameter from about 0.5 millimeters (mm) to about 5 millimeters (mm).

With reference to FIG. 3, the arcuate portion 24 can be formed to enable the arm 16 to fit around the femoral head F. In one example, the arcuate portion 24 can extend along an arc defined by a circle having a diameter of about 10 centimeters (cm) to about 28 centimeters (cm). The arc length can be from about 15 degrees to about 44 degrees. It should be understood, however, that the measurements provided herein for the arcuate portion 24 are merely exemplary, as the arcuate portion 24 can have any suitable arcuate shape for fitting around the femoral head F. Generally, the arcuate configuration can allow the distal tip 26 to engage the articulating surface of the femoral head F while the handle 18 is accessible exterior to anatomy.

With reference to FIGS. 1-3, the handle 18 can provide the user with a gripping surface S for the performance of the surgical procedure. Although not illustrated herein, the gripping surface S can be configured to facilitate grasping by the user, and thus, can include a knurled portion, raised portion, coating, etc. The handle 18 can include a proximal end 34 and a distal end 36. The proximal end 34 and the distal end 36 of the handle 18 can extend along the longitudinal axis L of the handle 18. With reference to FIG. 2, the proximal end 34 can be couplable to the impaction member 14, and the distal end 36 can be coupled to the proximal end 20 of the pick 12. The proximal end 34 can include a bore 38, which can receive a portion of the impaction member 14 to couple the impaction member 14 to the handle 18. In one example, the bore 38 can be sized to create a press-fit between the impaction member 14 and the handle 18, however, the bore 38 could include one or more internal features configured to mate with corresponding features on the impaction member 14, such as an internal lip, protrusion, threads, etc. Alternatively, the impaction member 14 could be coupled to the handle 18 through the use of one or more mechanical fasteners, etc.

With reference to FIGS. 1-3, the impaction member 14 can comprise any device suitable for applying a force in a direction of the arrow so that the distal tip 26 of the pick 12 can form the holes 30 in the femoral head F. In one example, the impaction member 14 can comprise a strike plate 40. As the strike plate 40 can be commercially available from Biomet Manufacturing Corporation of Warsaw, Indiana, the strike plate 40 will not be discussed in detail herein. Briefly, however, with reference to FIG. 2, the strike plate 40 can comprise a connecting portion 42, a graspable portion 44 and a strike portion 46. The connecting portion 42 can couple the strike plate 40 to the handle 18 of the pick 12. In one example, the connecting portion 42 can comprise a cylindrical rod, which can be press fit or threaded into the bore 38 of the handle 18.

The graspable portion 44 can comprise an undulating surface that facilitates gripping of the strike plate 40 during the surgical procedure. The graspable portion 44 can be formed between the connecting portion 42 and the strike portion 46. The strike portion 46 can be positioned adjacent to the graspable portion 44, and can extend transverse to the handle 18, and can be substantially perpendicular to a longitudinal axis L of the handle 18. With reference to FIG. 3, the strike portion 46 can have an enlarged planar strike surface 48, which can enable the user to contact the strike surface 48 with a second surgical instrument, such as a mallet 49. The strike surface 48 can be orientated such that when a force 50 in the direction of the arrow is applied to the strike surface 48, the distal tip 26 moves in the direction of the force 50 to form the holes 30 in the femoral head F.

In another example, with reference to FIGS. 1 and 2, the impaction member 14 can comprise a slap hammer 52. As the slap hammer 52 can be commercially available from Biomet Manufacturing Corporation of Warsaw, Indiana, the slap hammer 52, will not be discussed in detail herein. Briefly, however, the slap hammer 52 can include a shaft 54 and a collar 56. The shaft 54 can have a connecting portion 58 at a distal end 60 and a proximal stop 62 at a proximal end 64. The connecting portion 58 can couple the slap hammer 52 to the bore 38 of the handle 18. In one example, the connecting portion 58 can comprise a cylindrical rod, which can be sized to be press-fit or threaded into the bore 38.

The proximal stop 62 can comprise a cylindrical portion having a diameter greater than a diameter of the shaft 54. The proximal stop 62 can be sized to contact the collar 56 to prevent the further movement of the collar 56. The collar 56 can be slidable over the shaft 54 between the handle 18 and the proximal stop 62 when the slap hammer 52 is coupled to the pick 12. The collar 56 can include a graspable portion 66, which can be gripped by the user to move the collar 56 along the shaft 54. The collar 56 can be slid into the proximal stop 62 and the contact between the proximal stop 62 and the collar 56 can create a force 68. The application of the force 68 can cause the distal tip 26 to move in the direction of the force 50 to form the holes 30 in the femoral head F.

With reference to FIG. 2, it should be noted that although the microfracture pick system 10 is described and illustrated herein as comprising a strike plate 40 and a slap hammer 52, the microfracture pick system 10 could include only one of the strike plate 40 and slap hammer 52. Further, if desired, the strike plate 40 and the slap hammer 52 could be provided with the pick 12 in a surgical kit, to enable the user to select the desired impaction member 14 prior to performance of the surgical procedure. Thus, in one example, in order to assemble the pick 12 to the impaction member 14, the user can select the strike plate 40 or the slap hammer 52. The connecting portion 42, 58 of the selected one of the strike plate 40 or slap hammer 52 can be coupled to the bore 38 of the handle 18 of the pick 12.

Referring to FIG. 3, with the pick 12 assembled to the impaction member 14, an incision 80 can be made into the anatomy near to the femoral head F to perform a surgical procedure. Then, the pick 12 can be inserted into the anatomy from a lateral position, for example, until the distal tip 26 of the pick 12 is in contact with the femoral head F. The taper of the distal tip 26 can assist in an atraumatic entry into the anatomy by sliding over the femoral head F and gradually descending into a selected position. The impaction member 14 can then be impacted to create the hole 30 in the femoral head F. For example, if the strike plate 40 is coupled to the impaction member 14, then a second surgical instrument, such as the mallet 49, can impart the force 50 on the strike portion 46. The force 50 can cause the distal tip 26 to move towards the handle 18, thereby forming the hole 30 in the femoral head F. This process can be repeated to form a selected number of holes 30 in the femoral head F.

With reference to FIGS. 1 and 2, in the example of the slap hammer 52 being coupled to the pick 12, the collar 56 can be positioned adjacent to the handle 18 and then moved forcefully into contact with the proximal stop 62 to generate the force 68. The force 68 can cause the distal tip 26 to move towards the handle 18, thereby forming the hole 30 in the femoral head F. This process can be repeated to form a selected number of holes 30 in the femoral head F.

The formation of the holes 30 in the femoral head F can repair cartilage defects in the femoral head F. In this regard, the creation of the holes 30 can cause bone marrow and blood cells to come to the surface of the femoral head F. The bone marrow and blood cells can create a blood clot, which can lead to the formation of fibrocartilage in the area of the microfractures or holes 30.

Figure 4:
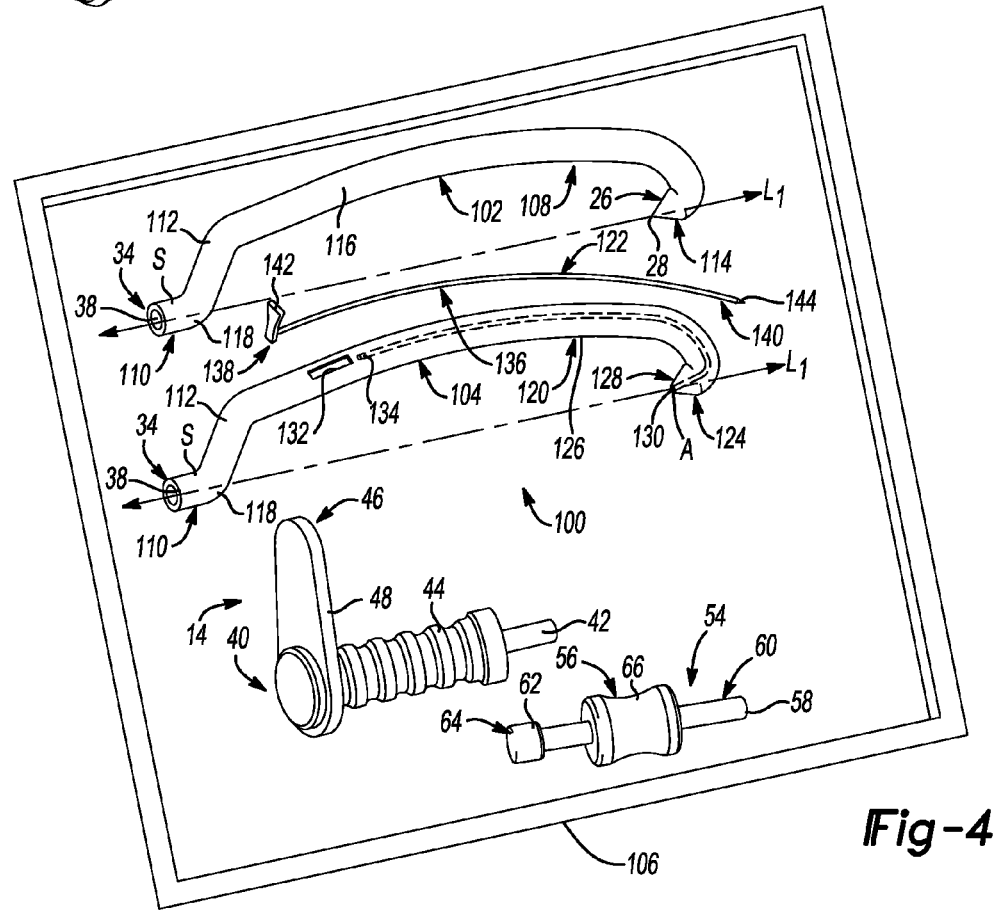
FIG. 4 is a perspective view of a kit containing an exemplary microfracture pick system for use with a femoral head according to the present teachings.
Figure 5:
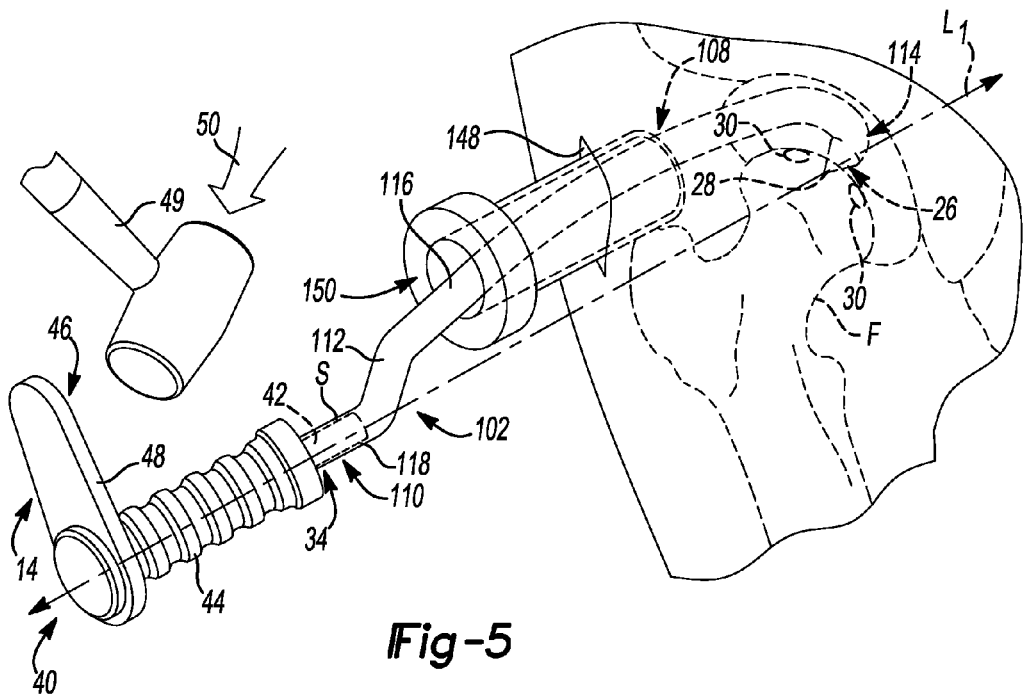
FIG. 5 is a schematic environmental illustration of an exemplary assembly of one of the microfracture pick systems of FIG. 4 being used to perform a procedure on a femoral head.
Figure 6:
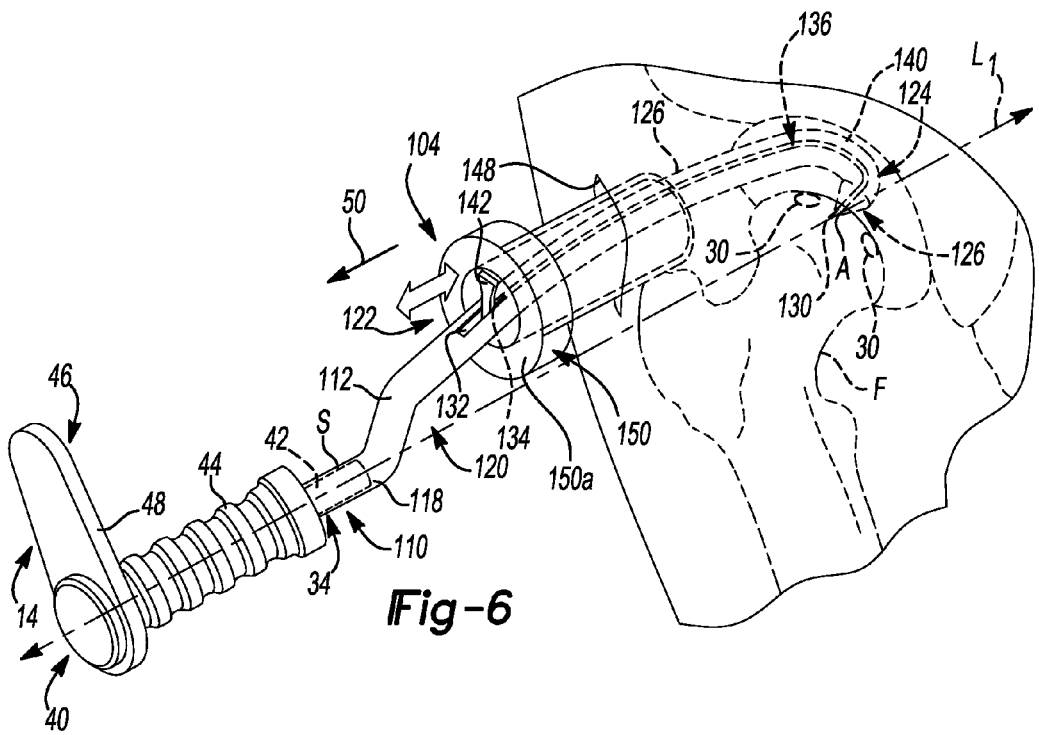
FIG. 6 is a schematic environmental illustration of an exemplary assembly of one of the microfracture pick systems of FIG. 4 being used to perform a procedure on a femoral head.

With reference now to FIGS. 4-6, in one example, a microfracture pick system 100 can be employed to repair a damaged portion of an anatomy. As the microfracture pick system 100 can be similar to the microfracture pick system 10 described with reference to FIGS. 1-3, only the differences between the microfracture pick system 10 and the microfracture pick system 100 will be discussed in great detail herein, and the same reference numerals will be used to denote the same or similar components. With reference to FIG. 4, the microfracture pick system 100 can include can include a pick 102, a retractable pick 104 and the impaction member 14. The pick 102, retractable pick 104 and the impaction member 14 can be provided as a surgical kit 106, however, it should be understood that the pick 102 and retractable pick 104 can be provided assembled to a desired impaction member 14 individually for use in a surgical procedure.

Referring to FIGS. 4 and 5, the pick 102 can include a member or arcuate arm 108 and a graspable portion or handle 110. The pick 102 can be composed of any suitable biocompatible material, such as a biocompatible metal or polymer. For example, the pick 102 can be composed of a stainless steel. In one example, the arm 108 can be integrally formed with the handle 110. It should be noted, however, that the arm 108 and the handle 110 could be discretely formed and coupled via any suitable technique, such as the use of mechanical fasteners, threading the arm 108 into an internally threaded bore on the handle 110 or vice versa, welding, etc.

The arm 108 can be shaped to fit around the femoral head F, and can be sized to be used in a low or minimally invasive procedure, as will be discussed herein (FIG. 5). The arm 108 can include a proximal end 112, a distal end 114 and an elongate portion 116. The proximal end 112 can be coupled to the handle 110. The proximal end 112 can include a slope, which can transition the elongate portion 116 into the handle 110. The distal end 114 can be positioned opposite the proximal end 112 and can lie along a longitudinal axis L1 of the handle 110. The distal end 114 can include the distal tip 26 and can be coupled to the elongate portion 116. The elongate portion 116 can have a slight, shallow curve, which can enable the elongate portion 116 to be used in a low or minimally invasive procedure, while still fitting around the femoral head F when positioned from a lateral position. In one example, the elongate portion 116 can extend along an arc defined by a circle having a radius of about 65 centimeters (cm) to about 114 centimeters (cm). It should be understood, however, that the measurements provided herein for the elongate portion 116 are merely exemplary, as the elongate portion 116 can have any suitable arcuate shape for fitting around the femoral head F.

The handle 110 can provide the user with the gripping surface S for performing the surgical procedure. The handle 110 can include the proximal end 34 and a distal end 118. The proximal end 34 and the distal end 118 of the handle 110 can extend along the longitudinal axis L1 of the handle 110. The proximal end 34 can be coupled to the impaction member 14, and the distal end 118 can be coupled to the proximal end 112 of the pick 102.

With reference to FIGS. 4 and 6, as the retractable pick 104 can be similar to the pick 102 described with reference to FIGS. 4 and 5, only the differences between the pick 102 and the retractable pick 104 will be discussed in great detail herein, and the same reference numerals will be used to denote the same or similar components. The retractable pick 104 can include a member or arcuate arm 120, a retractable tip 122 and the handle 110. The retractable pick 104 can be composed of any suitable biocompatible material, such as a biocompatible metal or polymer. For example, the retractable pick 104 can be composed of a stainless steel. In one example, the arm 120 can be integrally formed as one unitary piece with the handle 110. It should be noted, however, that the arm 120 and the handle 110 could be discretely formed and coupled via any suitable technique, such as the use of mechanical fasteners, threading the arm 120 into an internally threaded bore on the handle 110 or vice versa, welding, etc.

The arm 120 can be shaped to fit around the femoral head F, and can be sized to be used in a low or minimally invasive procedure, as will be discussed herein. The arm 120 can include the proximal end 112, a distal end 124 and an elongate portion 126. The distal end 124 can be positioned opposite the proximal end 112 and can lie along a longitudinal axis L1 of the handle 110. The distal end 124 can include a distal tip 128, and can be coupled to the elongate portion 126. The distal tip 128 can terminate at an apex A of a cone 130. As will be discussed, a portion of the retractable tip 122 can extend beyond the apex A of the cone 130 and can be operable to form the holes 30 in the femoral head F.

The elongate portion 126 can have a slight, shallow curve, which can enable the elongate portion 126 to be used in a low or minimally invasive procedure, while still fitting around the femoral head F from a lateral approach. In one example, the elongate portion 126 can extend along an arc defined by a circle having a radius of about 65 centimeters (cm) to about 114 centimeters (cm). It should be understood, however, that the measurements provided herein for the elongate portion 126 are merely exemplary, as the elongate portion 126 can have any suitable arcuate shape for fitting around the femoral head F. The elongate portion 126 can include a slot 132 and a bore 134. The slot 132 can be formed adjacent to the proximal end 112. The slot 132 can receive a portion of the retractable tip 122 therethough, so that a user can control the operation of the retractable tip 122, as will be discussed. The slot 132 can be formed so as to be in communication with the bore 134. The bore 134 can extend from the slot 132 to the apex A of the cone 130 of the distal tip 128. Thus, the bore 134 need not extend entirely through the arm 120, however, it will be understood, that the bore 134 can extend through the entire arm 120, if desired, to enable the arm 120 to pass over a guide wire, for example. The bore 134 can receive at least a portion of the retractable tip 122 to enable the retractable tip 122 to move from a first, retracted position to a second, extended position, as will be discussed.

With continuing reference to FIGS. 4 and 6, the retractable tip 122 can move relative to the elongate portion 126 of the arm 120. The retractable tip 122 can be composed of a suitable biocompatible material, such as a biocompatible metal or polymer. In one example, the retractable tip 122 can be composed of stainless steel. As will be discussed, the use of the retractable tip 122, particularly in the retracted position, can allow the passage in an atraumatic manner of the distal tip 128 through the anatomy. The retractable tip 122 can include a body 136 having a proximal end 138 and a distal end 140. The body 136 can be substantially cylindrical, and can be sized to be slidably received within the bore 134 of the arm 120. The body 136 is also flexible, to enable the body 136 to pass through the portion of the bore 134 located in the distal end 124 of the arm 120.

The proximal end 138 can include a slider 142. The slider 142 can be configured to extend through the slot 132, beyond a surface of the elongate portion 126, to enable the slider 142 to be manipulated by the user. The manipulation of the slider 142 can cause the body 136 to move within the bore 134 of the elongate portion 126. In this regard, the distal end 140 can include a pointed tip 144, which can be used to form the holes 30 in the femoral head F. The slider 142 can be used to move the pointed tip 144 from the first, retracted position, in which the pointed tip 144 is contained wholly within the arm 120, to the second, extended position, in which the pointed tip 144 extends beyond the arm 120, in use, to create the holes 30 (FIG. 6). The pointed tip 144 can have a diameter between about 2.0 millimeters (mm) to about 3.0 millimeters (mm) such that the pointed tip 144 forms the holes 30 in the femoral head F with about a 2.0 millimeter (mm) to about a 3.0 millimeter (mm) diameter. It should be noted, however, that the pointed tip 144 can have any selected diameter to form any selected diameter hole 30, such as a diameter from about 0.5 millimeters (mm) to about 5 millimeters (mm). In addition, it should be noted that the pointed tip 144 can be tapered or substantially cylindrical to include the selected diameter.

In one example, with reference to FIGS. 4 and 5, in order to assemble the pick 102 to the impaction member 14, the user can select the strike plate 40 or the slap hammer 52. The connecting portion 42, 58 of the selected one of the strike plate 40 or slap hammer 52 can be coupled to the bore 38 of the handle 110 of the pick 102. In order to assemble the retractable pick 104, with reference to FIGS. 4 and 6, the distal end 140 of the retractable tip 122 can be inserted through the slot 132 and the retractable tip 122 can be advanced until the slider 142 is retained within the slot 132. The connecting portion 42, 58 of a selected one of the strike plate 40 or slap hammer 52 can be coupled to the bore 38 of the handle 110 of the retractable pick 104.

With reference to FIG. 5, in order to perform a low or minimally invasive procedure using the pick 102, with the pick 102 assembled to the impaction member 14, a small incision 148 can be made into the anatomy near the femoral head F. A cannula 150 can be inserted into the incision and positioned near or adjacent to the femoral head F. The cannula 150 can have an inner diameter of about 10 millimeters (mm). Then, the pick 102 can be inserted into and through the cannula 150 so that the distal tip 26 of the pick 102 is in contact with the femoral head F. The impaction member 14 can then be impacted to create the hole 30 in the femoral head F, as discussed above. This process can be repeated to form a selected number of holes 30 in the femoral head F.

Referring to FIG. 6, in order to perform a low or minimally invasive procedure using the retractable pick 104, with the retractable pick 104 assembled to the impaction member 14, the small incision 148 can be made into the anatomy near the femoral head F. The cannula 150 can be inserted into the incision and positioned near the femoral head F. With the retractable tip 122 in the first, retracted position, the retractable pick 104 can be inserted into and through the cannula 150 so that the distal tip 26 of the retractable pick 104 is adjacent to the femoral head F. Generally, about 15 centimeters (cm) of the retractable pick 104 can extend beyond an outermost surface 150a of the cannula 150, while about 25 centimeters (cm) of the retractable pick 104 can extend from the outermost surface 150a of the cannula 150 to the femoral head F. Once the retractable pick 104 is inserted into the cannula 150, the user can actuate the slider 142 to move the retractable tip 122 from the first, retracted position to the second, extended position. With the retractable tip 122 in the second, extended position, the impaction member 14 can be impacted to create the hole 30 in the femoral head F, as discussed above. This process can be repeated to form a selected number of holes 30 in the femoral head F.

Accordingly, the microfracture pick system 10, 100 can be used to repair damaged tissue in the anatomy, such as repairing cartilage defects in the femoral head. By forming a number of small holes 30 in the subchondral bone of the femoral head F, bone marrow and blood can come to the surface of the bone, thereby promoting fibrocartilage growth. The microfracture pick system 10 can be used in a more open procedure, while the microfracture pick system 100 can be used in a low or minimally invasive procedure, providing a surgeon with a variety of options to suit the needs of various patients. It is understood, that each microfracture pick system 10, 100 can be used in an open procedure. The configuration of the arm 108, 120, however, can reduce the tissue disruption compared to the other configurations.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed:

1. A microfracture pick system for repairing cartilage on a femoral head, comprising:
    a handle having a distal end; and
    a curved pick connected to the distal end of the handle, the curved pick comprising a tip extending toward the handle and configured to make a depression in a femoral head surface located on an opposite side of the femoral head relative to the handle during a selected procedure.

2. The system of claim 1, wherein the tip extends along a longitudinal axis of the handle and opposed to the handle.

3. The system of claim 1, wherein the tip is a retractable tip.

4. The system of claim 3, the curved pick further comprising a slider configured to communicate a force from external to the femoral head to the retractable tip parallel to a longitudinal axis of the handle.

5. The system of claim 4, wherein the force moves the retractable tip between a first position and a second position.

6. The system of claim 5, wherein the retractable tip further comprises a pointed tip; and in the first position, the pointed tip is wholly contained within the curved pick, and in the second position, the pointed tip extends beyond the curved pick.

7. The system of claim 1, wherein the curved pick is configured to encompass opposing sides of a femoral head.

8. The system of claim 1, wherein the handle further comprises a driving member opposing the curved pick configured to transfer force external from the curved pick to the curved pick.

9. A method for repairing cartilage on a femoral head, comprising:
    making an incision in an anatomy near the femoral head;
    inserting a pick through the incision so that a distal tip of an arcuate arm of the pick is positioned near an articulating surface of the femoral head, wherein the pick has a handle and the arcuate arm is coupled to the handle, wherein the distal tip is formed on the arcuate arm and the distal tip extends towards the handle along a longitudinal axis of the handle; and
    impacting an impaction member coupled to an end of the handle such that a force from the impact causes the distal tip to contact the femoral head.

10. The method of claim 9, wherein impacting an impaction member further comprises:
    applying a force to a strike surface of a strike plate coupled to the handle.

11. The method of claim 9, wherein impacting an impaction member further comprises:
    sliding a collar of a slap hammer coupled to the handle against a proximal stop of the slap hammer.

12. The method of claim 9, further comprising:
    extending a distal tip from a distal end of the arcuate arm after the inserting the pick through the incision and prior to the impacting the impaction member;
    wherein the extended distal tip creates a hole in the femoral head.

13. The method of claim 9, wherein impacting the impaction member yields a force in a direction towards the handle.

14. The method of claim 9, wherein the impaction member is a slap hammer having a shaft, a proximal stop, and a collar, the shaft extending from the proximal end of the handle along the longitudinal axis of the handle and the collar operable to slide along the shaft to impact the proximal stop.

15. A microfracture pick system o repairing cartilage on a femoral head, comprising:
    a member having a handle at a proximal end and having a distal end;
    a force receiving portion at the proximal end; and
    a curved pick connected to the distal end of the member, the curved pick having a tip extending toward the handle and configured to contact an opposing surface of a femoral head, the opposing surface positioned opposite a surface of the femoral head facing the handle.

16. The system of claim 15, wherein the tip is moveable within the member.

17. The system of claim 15, wherein the tip is a retractable tip.

18. The system of claim 17, wherein the tip is retractable into the distal end of the member.

19. The system of claim 15, further comprising:
    a force providing member moveable relative to the force receiving portion.

20. The system of claim 19, wherein the force receiving member is substantially perpendicular to a longitudinal axis of the member.

* * * * *